US00PP12929P2

(12) United States Plant Patent
Pieters

(10) Patent No.: US PP12,929 P2
(45) Date of Patent: Sep. 10, 2002

(54) CHRYSANTHEMUM PLANT NAMED 'VENICE'

(76) Inventor: Dirk Pieters, Schierveldestraat 3A, Oosnieuwkerke, 8840 Staden (BE)

( * ) Notice: Subject to any disclaimer, the term of this patent is extended or adjusted under 35 U.S.C. 154(b) by 0 days.

(21) Appl. No.: 09/550,155

(22) Filed: Apr. 17, 2000

(51) Int. Cl.[7] ..... A01H 5/00

(52) U.S. Cl. ..... Plt./295

(58) Field of Search ..... Plt./295

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new plant variety of chrysanthemum producing yellow anemone-type flowers.

1 Drawing Sheet

BACKGROUND OF THE INVENTION

The present invention is directed to a new and distinct variety of chrysanthemum morifolium. The varietal denomination of the new chrysanthemum is 'VENICE'.

The new variety is a cross of two unnamed, undistributed and unpatented seedlings. The new variety has been asexually reproduced by vegetative cuttings in Ventura County, Calif. and the distinguishing characteristics are retained through successive generations of asexual reproduction.

SUMMARY OF THE INVENTION

'VENICE' is a chrysanthemum plant that produces near white ray florets, yellow disc florets and an anemone-type flower.

The following is a comparison of the new variety to a commercial variety named 'GEDI YT8' (U.S. Plant Pat. No. 11,725:

| 'GEDI YT8 | VENICE | | UNNAMED SEED PARENT | UNNAMED POLLEN PARENT |
|---|---|---|---|---|
| Inflorescence Diameter | About 4.8 cm | About 3 cm | About 3 cm | About 5 cm |
| Ray Floret coloration when mature | Near 12 B | Near 16 D | Different color ray florets | Different color ray florets |
| Natural bloom date | 1st week of October | 3rd week of September | 1st week of October | 2nd week of September |
| Quantity of inflorescence per stem | About 15 | About 20 | About 22 | About 15 |

BRIEF DESCRIPTION OF ILLUSTRATIONS

The accompanying photograph shows a typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. Plants described are approximately 65 days old from a rooted cutting. 'VENICE' has not been observed under all possible environmental conditions. The phenotype may vary with variations in the environment such as temperature, light intensity, day length and cultural conditions. The color desiganations herein are from The Royal Horticultural Society Colour Chart except where general terms are used.

To produce a commercial product the plants may be pinched once about ten days after planting. No growth retardant has been applied in the specimens described. Useful growing conditions include average night temperatures of about 17° C. to 20° C. and average day temperatures of about 20° C. to 30° C. No susceptibility or resistance to disease has been observed. Resistence and susceptibility to insects have not been observed. Seed production has not been observed. Winter hardiness has not been observed.

Rooting characteristics:
- *Time to initiate roots.*—About 7 to 14 days at about 21° C.
- *Root description.*—Fine, fibrous.

Plant:
- *Plant type.*—Herbaceous perennial.
- *Growth habit.*—Mounding.
- *Size.*—Height about 21 cm, width about 20 cm.
- *Growth rate.*—Moderate.
- *Branching characteristics.*—Very free branching, lateral branches are about 18 cm long. 0.5 cm in diameter and near 136C in color.

Foliage:
- *Arrangement.*—Alternate.
- *Compound or simple.*—Simple.
- *Quantity of leaves.*—Many.
- *Leaf size.*—Length: About 5 cm. Width: About 3 cm.
- *Leaf shape.*—Ovate.
- *Leaf tip.*—Acuminate.
- *Leaf base.*—Attenuate.
- *Leaf attachment.*—Stalked.
- *Petiole.*—Length about 2 cm, diameter about 0.2 cm, color near 136C.
- *Margin type.*—Serrate.
- *Texture.*—Lightly pubescent.
- *Color.*—Young foliage upper side: Near 137C. Young foliage under side: Near 137C. Mature foliage upper side: Near 137A. Mature foliage under side: Near 137B.

*Venation*.—Net. Color: Upper side: Near 137C. Under side: Near 137D.

Bloom:

*Inflorescence*.—Flowering habit: Induced by darkness period greater than 13.5 hours. Approximately 50 days of day length required to induce and develop blooms. Inflorescence form: Daisy. Natural flowering season: Around the $2^{nd}$ and $3^{rd}$ weeks in September in Ventura County, Calif. Quantity of inflorescences per stem: About 20. Inflorescence diameter: About 3 cm, ray florets are attached at approximately a 45° angle to the disc which makes the overall natural diameter of the inflorescence less than the sum of the parts when the inflorescence is dissected. Inflorescence depth: About 1.5 cm. Disc diameter: About 1.7 cm. Inflorescence longevity on plant: About 20 to 26 days. Persistence: Persistent.

*Ray florets*.—Appearance: Matte. Texture: Smooth. Number: About 40 to 50. Shape: Oblanceolate. Margin: Entire. Tip: Obtuse. Length: About 1.5 cm. Width: About 0.5 cm. Color: Upper side: First opening: Near 15C, frequently stripes of near 155A occur on the upper mature and fading ray florets. Mature: Near 16D. Fading: Near 16D. Under side: First opening: Near 14C. Mature: Near 16C. Fading: Near 15D.

*Disc florets*.—Appearance: Shiny. Texture: Smooth. Number: Over 100. Shape: Cylindric. Tip: Obtuse. Length: About 0.8 cm. Width: About 0.1 cm. Color: First opening: Near 13B. Mature: Near 14C. Fading: Near 16B.

*Peduncle*.—Diameter about 0.3 cm. Length: Terminal, shortest: About 2 cm. Lateral, longest: About 5 cm. Color: Near 138A. Strength: Moderate. Habit: Erect.

*Inflorescence bud*.—Length: About 0.8 cm. Diameter: About 1 cm. Form or shape: Globular. Color: Near 13B.

*Involucral bracts*.—Length about 0.4 cm, width about 0.2 cm. Appearance: Matte. Texture: Lightly pubescent. Number: About 20 to 30. Shape: Ovate. Margin: Entire. Tip: Acute. Color: Upper side: Near 138A. Under side: Near 138A.

Reproductive organs:

*Ray florets*.—Pistillate: Length about 0.8 cm. Pistil number: 1 per flower. Stigma shape: 2 branched. Stigma color: Near 7D. Style length: About 0.6 cm. Style color: Near 6D.

*Disc florets*.—Pistillate: Length about 0.6 cm. Pistil number: 1 per flower. Stigma shape: Cylindric. Style length: About 0.5 cm.

*Staminate*.—Stamen number: About 5. Anther shape: Tubular. Anther color: Near 14C. Pollen color: Near 16A.

What is claimed is:

1. A new and distinct chrysanthemum plant of the variety substantially as herein shown and described.

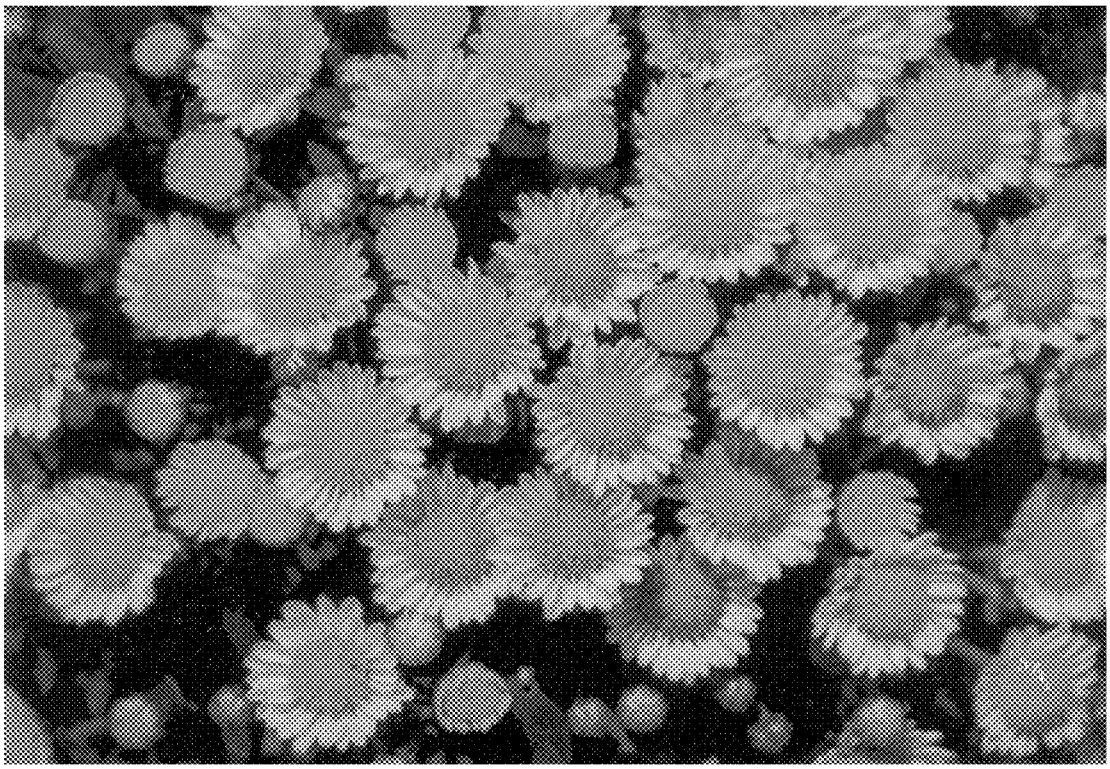

* * * * *